United States Patent [19]

Konagaya

[11] Patent Number: 5,410,493
[45] Date of Patent: Apr. 25, 1995

[54] METHOD AND DEVICE FOR EVALUATING A DECISION CONDITION WITH SEQUENCE MOTIFS USED FOR DISCRIMINATION OF SYMBOL SEQUENCES

[75] Inventor: Akihiko Konagaya, Tokyo, Japan

[73] Assignee: NEC Corporation, Tokyo, Japan

[21] Appl. No.: 755,364

[22] Filed: Sep. 6, 1991

[51] Int. Cl.⁶ .............................................. G06F 15/46
[52] U.S. Cl. .................................. 364/496; 364/499; 364/554; 395/600
[58] Field of Search ............... 364/554, 496, 497, 499; 395/600

[56] References Cited

U.S. PATENT DOCUMENTS

| | | | |
|---|---|---|---|
| 4,823,306 | 4/1989 | Barbic et al. | 395/600 |
| 4,872,122 | 10/1989 | Altschuler et al. | 364/554 |
| 4,933,883 | 6/1990 | Pennebaker et al. | 364/554 |
| 5,263,159 | 11/1993 | Mitsui | 395/600 |

Primary Examiner—Emanuel Voeltz
Assistant Examiner—Eric W. Stamber
Attorney, Agent, or Firm—Foley & Lardner

[57] ABSTRACT

For evaluating decision conditions, by the MDL principle, used for discriminating a given amino acid sequence as a particular one of super families, a sum of the description lengths of each of the decision conditions and a precision of each decision condition is calculated to make an evaluating parameter. Each decision condition comprises a plurality of conditional clauses. A description length of the decision condition is given by a total of clause description lengths of the conditional clauses. One of the clause description lengths is given by a total of a description length of the particular super family and a description length of one or more sequence motifs and a distance between motifs contained in the clause. An optimum is determined as one of the decision condition which makes the minimum evaluating parameter.

3 Claims, 6 Drawing Sheets

FIG. 1

```
CCTE     GPKEPEVTVPEGDASAGRDI FDSQCSACHAIEG--DSTAAPVLGGVIGRKAGQEK-FAYSKGMKG
CCRF2G   ----GSAPPGDPVEGKHLFHTICILCHTDIKG-RNKVGPSLYGVVGRHSGIEPGYNYSEANIK
CCAG2    --------EGDVAKGEAAF-KRCSACHAIGEGAKNKVGPSLYGVVGRHSGIEPGYNYSEANIK
CCRD2    --------AGDPVKGEQVF-KQCKICHQVGPTAKNGVGPEQNDVFGQKAGARPGFNYSDAMKN
CCRF2V   --------ODAASGEQVF-KQCLVCHSIGPGAKNKVGPVLNGLFGRHSGTIEGFSYSDANKN
CCRF2A   --------AGDPDAGQKVF-LKCAACHKIGPGAKNGVGPSLNGVANRKAGQAEGFAYSDANKN
CCNA5A   --------GDVEAGKAAF---NKCKACHEIGESAKNKVGPELDGLDGRHSGAVEGYAYSPANKA
CCQF2F   ---------ADAPT----AF---NQCKACHSIEAG--KNGVGPSLSGAYGRKVGLAPNYKYSAAHLA
CCQF2M   ---------ADAPPP---AF---NQCKACHSIDAG--KNGVGPSLSGAYGRKVGLAPNYKYSPAHLA
CCQFM2   ---------ADAPAG----F-TLCKACHSVEAG--KNGVGPSLAGVYGRKAGTISGFKFSDPHIK
CCQFF2   ---------ADAPP----AF-GMCKACHSVEAG--KNGVGPSLAGVYGRKAGTLAGFKFSDPHAK

....D.......F....C..CH............P.........G........S......
```

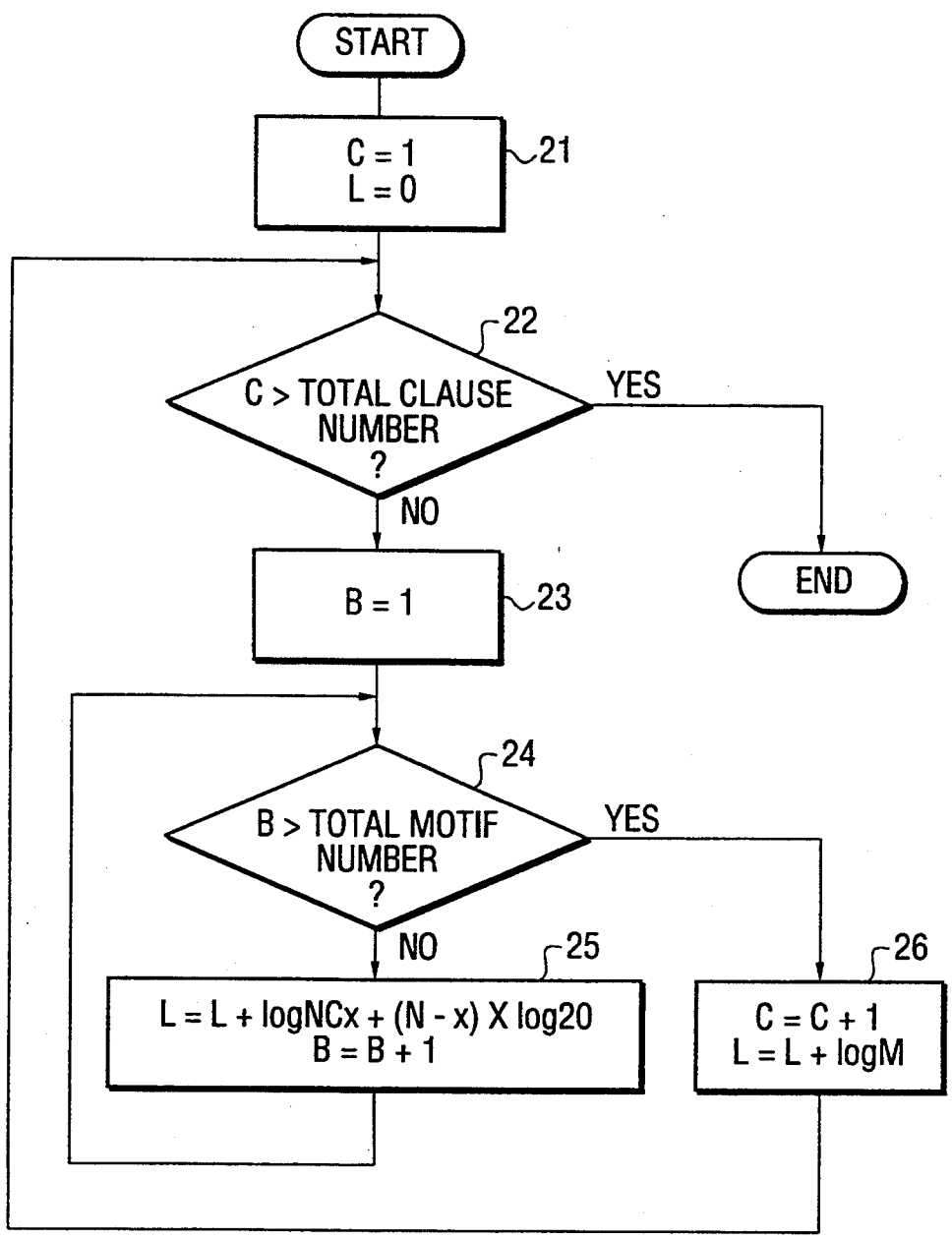

FIG. 6

| CLAUSE NUMBER | ITEM NUMBER | ITEM (MOTIF) |
|---|---|---|
| 1 | 1 | CX x CH |
|  | 2 | PG x KM |
|  | 3 |  |
|  | ⋮ |  |
| 2 ⋮ | ⋮ | ⋮ |

METHOD AND DEVICE FOR EVALUATING A DECISION CONDITION WITH SEQUENCE MOTIFS USED FOR DISCRIMINATION OF SYMBOL SEQUENCES

BACKGROUND OF THE INVENTION

The present invention relates to a method and a device for evaluating a decision condition with sequence motifs used for discrimination of symbol sequences such as amino acid sequences, DNA sequences and other sequences composed of symbols aligned in series.

The symbol sequences can be classified into a plurality of groups or categories so that each of the categories contains symbol sequences related to each other. The majority of the symbol sequences in one category can have one or more common symbol sequence portions or patterns. Such common patterns are called sequence motifs.

For example, proteins are known as various sequences of amino acids. Twenty (20) symbols, that is, A, C, D, E, F, G, H, I, K, L, M, N, P, Q, R, S, T, V, W, and Y are used to denote twenty amino acids, respectively, and amino acid sequences are represented as symbol sequences by use of those symbols. Proteins or amino acid sequences are classified into a plurality of super families or categories of functionally related proteins. The majority of the amino acid sequences classified in one category have one or more sequence motifs which represent conserved amino acid residues. For example, a pattern "CXXCH" is known as a common pattern or a sequence motif for amino acid sequences in the cytochrome c which is a super family of proteins. Here, "C" and "H" represent amino acids as described above and "X" represents an arbitrary one of twenty amino acids.

Those sequence motifs can be used as indexes for discriminating given symbol sequences and/or for predicting categories of unknown symbol sequences. That is, the sequence motifs are used in the decision condition for discriminating symbol sequences.

When those sequence motifs are used as the indexes for the decision condition, an inference rule is described as a decision predicate including the sequence motif or motifs. An example of the decision predicate is as follows: "If the given symbol sequence contains sequence motif CXXCH, the symbol sequence corresponds to cytochrome c . . . " However, it is very hard to find such a deterministic inference rule, because of the existence of noise, or uncertainty, due to the variety of biological species.

An actual amino acid sequence data bank (PIR 18.0) has 6158 sequences registered. 189 sequences therein have the sequence motif CXXCH but 119 sequences are classified in cytochrome c. Accordingly, the sequence motif CXXCH does not make a complete decision condition for discriminating amino acid sequences as category of cytochrome c. Another sequence motif can be used as the index in place of CXXCH or in combination with CXXCH, but cannot give the complete decision condition because of the noise or uncertainty.

To overcome the difficulty, the following type of rule is more appropriate to express the decision predicate with probability as follows: "If the given sequence contains the motif "CXXCH", it corresponds to cytochrome c with probability 4/5, but otherwise with probability 1/5".

Accordingly, sequence motifs are not always present in all of symbol sequences classified in one category but are present with certain probabilities.

Distance information between two sequence motifs are known to be used as an item of the decision condition.

Therefore, a plurality of decision condition can be made for discriminating a given symbol sequence as one of categories, according to use of sequence motifs and the distance information.

It is desired to evaluate those decision conditions in order to select the optimal one of those decision conditions.

It is another problem to select optimal motifs used in the decision predicates.

SUMMARY OF THE INVENTION

It is an object of the present invention to provide a method and a device for evaluating a decision condition with sequence motifs according to the Minimum Description Length (MDL) principle.

According to the present invention, a method is obtained for evaluating a decision condition used for discrimination of a given symbol sequence as a particular one of a plurality of categories, each of the categories containing a plurality of symbol sequences related to each other, the related symbol sequences having common sequence portions as sequence motifs with probabilities, the decision condition comprising at least one of the sequence motifs. The method comprises: calculating a description length of the decision condition as a first value, calculating a description length of a known precision of the decision condition as a second value; and summing the first and the second values to make a sum, the decision condition being evaluated by the sum.

When the decision condition comprises a plurality of conditional clauses, description lengths of the plurality of conditional clauses are individually calculated as clause description lengths, and the first value being given by a total of the clause description lengths.

When a particular one of the conditional clauses has at least one of the sequence motifs, a description length of the particular conditional clause is given as a particular one of the clause description lengths by a total of a description length of the at least one sequence motif and a description length of the particular category.

When a particular one of the conditional clauses has two sequence motifs different from each other and a distance between the two sequence motifs, a description length of the particular conditional clause is given as a particular one of the clause description lengths by a total of description lengths of the two sequence motifs, the distance, and the particular category.

The known precision is given by a probability distribution of a number of symbol sequences which are known to fulfill the decision condition in known data of symbol sequences.

The known precision is preferably calculated by use of an entropy function from the probability distribution.

According to the present invention, a device is obtained for evaluating a decision condition used for discrimination of a given symbol sequence as a particular one of a plurality of categories, each of the categories containing a plurality of symbol sequences related to each other, the related symbol sequences having common sequence portions as sequence motifs with probabilities, the decision condition comprising at least one of the sequence motifs. The device comprises: input means for inputting the decision condition as an input data signal; analyzing means coupled to the input means for analyzing the input data signal to produce an analyzed data signal; input memory means coupled to the analyzing means for memorizing the analyzed data signal; data memory means for memorizing a set of known data of the categories, the symbol sequences, and the sequence motifs; calculating means coupled to the input memory means and the data memory means responsive to the analyzed data signal for calculating a description length of the decision condition as a first value, the calculating means calculating, as a second value, a description length of a precision of the decision condition from the known data, the calculating means calculating a sum of the first and the second values to produce an evaluation parameter; and control means coupled to the input memory means, the data memory means, and the calculating means for controlling calculating operation of the calculating means.

BRIEF DESCRIPTION OF THE DRAWINGS

FIG. 1 is a view illustrating a plurality of amino acid sequences;

FIG. 2 is a flow chart illustrating calculation of a description length of motifs;

FIG. 6 is a view illustrating contents of an input memory in FIG. 5.

DESCRIPTION OF PREFERRED EMBODIMENTS

Figure 3:
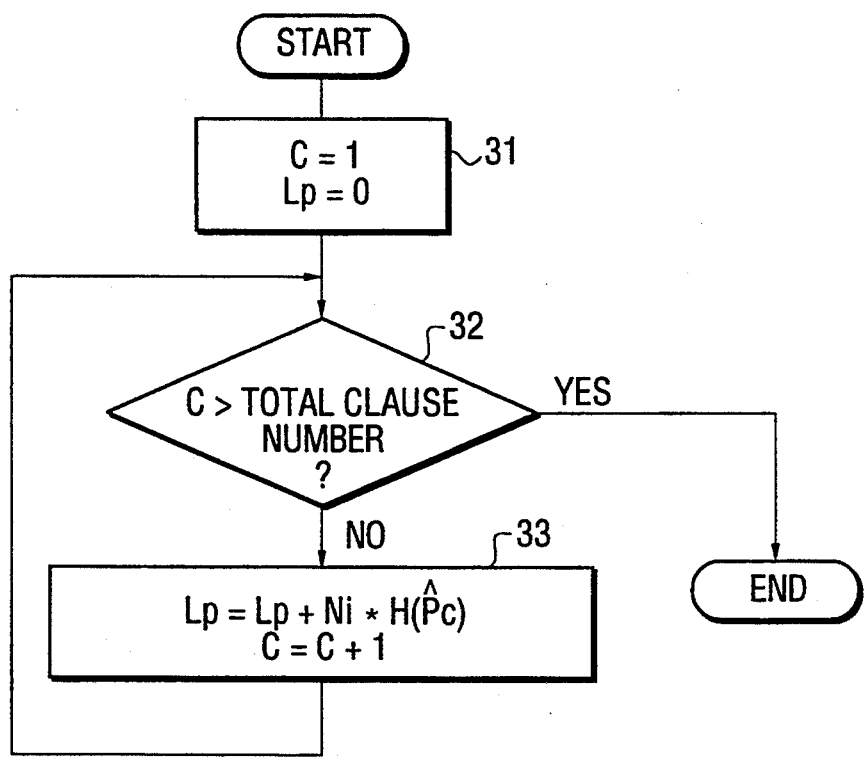
FIG. 3 is a flow chart illustrating calculation of a description length of a precision of the motifs.

Embodiments of the present invention will be described in connection with amino acid sequences below.

A plurality of amino acid sequences are exemplarily shown in FIG. 1 by use of a set of twenty symbols described in the preamble. In the figure, names of amino acid sequences such as CCTE, CCRF2G and others are shown at 10 on the left side, the corresponding amino acid symbol sequences are shown at 11 on the right side of the names 10. Those amino acid symbol sequences are arranged by use of vacant marks "-" so that amino acids common in those sequences are aligned in individual vertical lines. The common amino acids are shown as a common array 12 with periods (.) which represent absence of common amino acids.

EXAMPLE 1

Now, description will be made as to decision predicates of the decision conditions for discriminating a given amino acid sequence "J" as cytochrome c by the use of motifs CXXCH, PGXKM, and AAQCH.

DECISION PREDICATE 1

This predicate 1 means that the sequence "J" corresponds to cytochrome c if it contains the pattern of the sequence motif "CXXCH", but it is otherwise if it does not contain the pattern. This decision predicate 1 is briefly expressed by two clauses as follows:

$$\left\{ \begin{array}{l} \text{motif (J, cytochrome c): contain ("CXXCH", J).} \\ \text{motif (J, otherwise).} \end{array} \right.$$

DECISION PREDICATE 2

This decision predicate means that the sequence "J" corresponds to cytochrome c if it contains both patterns of sequence motifs "CXXCH" and "PGTKM" but it is otherwise if it does not contain the both patterns. This is also expressed as follows:

$$\left\{ \begin{array}{l} \text{motif (J, cytochrome c): contain ("CXXCH", J),} \\ \text{contain ("PGXKM", J).} \\ \text{motif (J, otherwise).} \end{array} \right.$$

DECISION PREDICATE 3

This decision predicate 3 means that the sequence "J" corresponds to cytochrome c if it contains the sequence motif "CXXCH" or "AAQCH", but it is otherwise if it contains neither "CXXCH" nor "AAQCH". This decision predicate is expressed by three clauses as follows:

$$\left\{ \begin{array}{l} \text{motif (J, cytochrome c): contain ("CXXCH", J).} \\ \text{motif (J, cytochrome c): contain ("AAQCH", J).} \\ \text{motif (J, otherwise).} \end{array} \right.$$

Table 1 shows the distribution of 6158 training sequences in the data bank PIR 18.0 observed by the decision predicates 1, 2, and 3.

TABLE 1

| Clauses | Total number of sequences | Number of targets | Number of correct sequences |
|---|---|---|---|
| Decision Predicate 1 | | | |
| CXXCH | 6158 | 189 | 116 |
| otherwise | 5969 | 5969 | 5966 |
| Decision Predicate 2 | | | |
| CXXCH and PGTKM | 6158 | 78 | 78 |
| otherwise | 6080 | 6080 | 6039 |
| Decision Predicate 3 | | | |
| CXXCH | 6158 | 189 | 116 |
| AAQCH | 5969 | 4 | 3 |
| otherwise | 5965 | 5965 | 5965 |

In order to evaluate decision conditions by the decision predicates 1, 2, and 3, a description length of the decision condition and a description length of precision of the decision condition are calculated according to the present invention.

The description length of the decision condition is given by the sum of description lengths of individual clauses in the decision predicate. The description length of each clause is given by the sum of a bit number necessary for encoding the category and a bit number necessary for encoding the items or the sequence motifs in the clause.

The bit number necessary for encoding the category is given by log M, where M is a number of categories. The bit number necessary for encoding the motifs is calculated in the following manner. When the sequence motif consists of N (integer) symbols and the sequence motif does not contain X, the sequence motif is one of $20^N$ symbol sequences because there are 20 amino acids. Therefore, the necessary bit number is given by N×log 20.

When the sequence motif contains "X", the necessary bit number is calculated by $\log {}_NC_x + (N-x) \times \log 20$. In the formula, x is a number of "X" in the sequence motif, ${}_NC_x$ is a number of combinations for selecting x positions from N positions in the sequence motif. Since 20 amino acids can be distributed in (N−x) positions, $20^{N-x}$ symbol sequences are encoded and the necessary bit number therefor is given by $(N-x) \times \log 20$.

Now, referring to FIG. 2, description will be made as regards calculation of the description length of the decision condition in connection with the decision predicate 2.

At first, the clause number C and the description length L are set 1 and 0, respectively, at step 21. At step 22, it is decided whether or not C exceeds the total number of clauses in the decision predicate. Since the decision predicate 2 has two clauses, step proceeds from 22 to 23. At step 23, an item number B is set 1. Then, it is decided at step 24 whether or not B exceeds the number of items or sequence motifs in the clause. Since the first clause in the decision predicate 2 has two items or sequence motifs, step proceeds from 24 to 25. At step 25, calculation is performed for the following equations:

$$L = L + \log {}_NC_x + (N-x) \times \log 20 \quad (1)$$

$$B = B + 1 \quad (2)$$

The first sequence motif "CXXCH" has five symbols and two "X". Therefore, the equations (1) and (2) are calculated as follows:

$$L = 0 + \log {}_5C_2 + (5-2) \times \log 20 = 16.3$$

$$B = 1 + 1 = 2$$

Thereafter, step returns from 25 to 24. B does not exceed the number (2) of items or sequence motifs in the first clause. Therefore, equations (1) and (2) are again calculated for the second second motif in the first clause at step 25. The second sequence motif "PGXKM" has five symbols and one X. Therefore, equations (1) and (2) are calculated as follows:

$$L = 16.3 + \log {}_5C_1 + (5-1) \times \log 20 = 35.9$$

$$B = 2 + 1 = 3$$

Then, step again returns from 25 to 24. Since B exceeds the item or sequence motif number in the first clause, step proceeds from 24 to 26. At step 26, the following equations (3) and (4) are calculated.

$$L = L + \log M \quad (3)$$

$$C = C + 1 \quad (4)$$

The number of categories or super families of proteins is about 1000. Thus, equations (3) and (4) are calculated by:

$$L = 35.9 + \log 1000 = 45.9$$

$$C = 1 + 1 = 2$$

Thereafter, step returns to 22 from 26. Since C does not exceed the total clause number, step proceeds from 22 to 23 and B is reset 1. The second clause does not have any motif, step proceeds to 26 from 24. The equations (3) and (4) are again calculated as follows:

$$L = 45.9 + \log 1000 = 55.9$$

$$C = 2 + 1 = 3$$

Then, it is decided at step 22 that C exceeds the total clause number. Accordingly, the calculation is completed and the description length of the decision condition by the decision predicate 2 are given by L=55.9 (bits).

The description length of precision of the decision condition is calculated by a bit number necessary for encoding the probability distribution of the number of sequences discriminated by each clause in the decision predicate.

It is provided that the number of sequences corresponding to an i-th clause in the decision predicate, the actual number of sequences corresponding to a desired category and the actual number of sequences excluded from the desired category are represented by Ni, Ni+ and Ni−, respectively. Ni is a sum of Ni+ and Ni−, that is, Ni=Ni+ +Ni−. The probability of the case is expressed by:

$$p_i^{Ni+} \times (1-p_i)^{Ni-},$$

where pi=Ni+/Ni.

The bit number necessary for encoding the probability is given by:

$$-\log p_i^{Ni+} \times (1-p_i)^{Ni-}.$$

Therefore, the total bit number Lp for all of the clauses in the decision predicate is expressed by:

$$L_p = \sum_i -\log p_i^{Ni+} \times (1-p_i)^{Ni-}.$$

Providing that $\hat{p}_i$ and $\bar{p}_i$ represent a maximum likelihood estimate of pi and a random variable, respectively, the total bit number Lp is rewritten as follows:

$$L_p = \sum_i N_i \times H(\bar{p}_i) + D(\bar{p}_i \| \hat{p}_i).$$

In the formula, $H(\bar{p}_i)$ and $D(\bar{p}_i \| \hat{p}_i)$ are an entropy function and an information amount by Kullbach-Leibler, respectively, as determined by the following equations:

$$H(\bar{p}) = -\bar{p} \log \bar{p} - (1-\bar{p}) \log (1-\bar{p})$$

$$D(\bar{p}_i \| \hat{p}_i) = \bar{p}_i \times (\log \bar{p}_i - \log \hat{p}_i) + (1-\bar{p}_i) \log (1-\hat{p}_i) - \log (1-\hat{p}_i).$$

Now, providing that $\hat{p}_i$ and $\bar{p}_i$ are approximately equal to each other, that is, $\bar{p}_i = \hat{p}_i = (Ni++1)/(Ni+2)$, the total bit number Lp can be approximately expressed by:

$$L_p = \sum_i N_i \times H(\hat{p}_i).$$

The equation of the total bit number Lp is a monotonous decreasing function. That is, Lp is large as $\hat{p}_i$ decreases to 0, but ecreases to 0 as $\hat{p}_i$ increases to 1.

The total bit number Lp expressed by the entropy function is considered minimum in view of encoding according to the Shanon's first law.

Now, referring to FIG. 3, description will be made as regards calculation of the description length of the precision of the decision condition in connection with the decision predicate 2.

At first, the clause number C and the description length Lp are set 1 and 0, respectively, at step 31. Then, it is decided at step 32 whether or not C exceeds the total clause number of the decision predicate. Since the total clause number is 2, step proceeds from 32 to 33.

At step 33, the following equations (5) and (6) are calculated:

$$Lp = Lp + Ni \times H(\hat{p}i) \quad (5)$$

$$C = C + 1 \quad (6)$$

According to the amino acid sequence data bank of PIR 18.0, 78 sequences of all of 6158 sequences actually have the both of sequence motifs "CXXCH" and "PGXKM", and all of the 78 sequences actually correspond to cytochrome c as shown at Decision predicate 2 in Table 2. It is provided from the actual data that N1 and $\hat{p}1$ are 78 and $(78+1)/(78+2)$, respectively. Therefore, equations (5) and (6) are calculated as follows:

$$Lp = 0 + 78 \times H(79/80) = 7.8 \text{ (bits)}$$

$$C = 1 + 1 = 2$$

Then, C is compared with the total clause number at step 32. Since C is not larger than the total clause number, equations (5) and (6) are calculated in connection with the second clause at step 33.

According to the data bank PIR 18.0, 6080 sequences do not have both of the motif patterns "CXXCH" and "PGXKM" and 6039 sequences of them do not correspond to cytochrome c as shown at Decision Predicate 2 in Table 1. Accordingly, N2 and $\hat{p}2$ are 6080 and $(6039+1)/(6080+2)$, respectively. Therefore, equations (5) and (6) are calculated as follows:

$$Lp = 7.8 + 6080 \times H(6040/6082) = 369.3 \text{ (bits)}$$

$$C = 2 + 1 = 3$$

Thus, the calculation is completed since C exceeds the total clause number, and the description length of the precision of the decision condition is given by 369.3 bits in connection with the decision predicate 2.

Similar calculations are performed for the decision predicates 1 and 3, and the results are shown in the following Table 2.

TABLE 2

| Decision predicate | Decision condition | Description Length | | |
|---|---|---|---|---|
| | | condition | precision | sum |
| 1 | CXXCH | 36.2 | 230.0 | 266.2 |
| 2 | CXXCH and PGXKM | 55.8 | 369.3 | 425.1 |
| 3 | CXXCH or PGXKM | 67.8 | 199.7 | 267.5 |

Table 2 shows that the use of the sequence motif "CXXCH" alone gives the minimum description length. Accordingly, it will be understood from the MDL principle that the sequence motif "CXXCH" is optimum as the decision condition for discrimination of cytochrome c.

In order to discriminate mitochondria cytochrome c, sequence motif "CXXCH", "PGXKM" and "AAQCH" are used in three decision predicates 1', 2', and 3' similar to the decision predicates 1, 2, and 3 and the description length are calculated by the similar way. The results are shown in Tables 3 and 4 corresponding to Tables 1 and 2, respectively.

TABLE 3

| Clauses | Total number of sequences | Number of targets | Number of correct sequences |
|---|---|---|---|
| Decision Predicate 1' | | | |
| CXXCH | 6158 | 189 | 70 |
| otherwise | 5969 | 5969 | 5966 |
| Decision Predicate 2' | | | |
| CXXCH and PGTKM | 6158 | 78 | 70 |
| otherwise | 6080 | 6080 | 6073 |
| Decision Predicate 3' | | | |
| CXXCH | 6158 | 189 | 70 |
| AAQCH | 5969 | 4 | 3 |
| otherwise | 5965 | 5965 | 5965 |

TABLE 4

| Decision predicate | Decision condition | Description Length | | |
|---|---|---|---|---|
| | | condition | precision | sum |
| 1 | CXXCH | 36.2 | 227.9 | 264.1 |
| 2 | CXXCH and PGXKM | 55.8 | 127.7 | 183.5 |
| 3 | CXXCH or PGXKM | — | — | — |

It will be understood from Table 4 that the use of sequence motifs "CXXCH" and "PGXKM" is optimum as the decision condition for discriminating mitochondria cytochrome c.

EXAMPLE 2

Another type of the decision predicate is known for discriminating sub-categories. The decision predicate of this type uses predicates of "search (P, J, R,)", "match (P, J, R)" and "any (Min, Max, J, R)".

The phrase "search (P, J, R)" means that when the sequence motif P is searched in the given sequence J, the residual portion of the given sequence is made as R, and back-tracking is performed.

The phrase "match (P, J, R)" means that when a leading pattern of the sequence J is corresponding to the sequence motif P, the residual portion of the sequence J is made as R.

The phrase "any (Min, Max, J, R)" means that a number of symbols are omitted from a leading symbol of the sequence J and the residual portion of the sequence J is made as R. The omitted sybol number is given by Min and Max as the minimum and the maximum numbers. Therefore, the back-tracking is repeated by (Max-Min) times.

Two examples of the decision predicate of this type are demonstrated below.

DECISION PREDICATE 4

```
motif (J, s-cytochrome c): search ("CXXCH",
    J, J1), search ("MP", J1, -).
```

-continued motif (J, otherwise)

This decision predicate 4 means that when the given sequence J has a first portion corresponding to the sequence motif "CXXCH" and has a second portion corresponding to the sequence motif "MP" in the following sequence portion after the first portion, the sequence J corresponds to the s-type cytochrome c. If the sequence J does not have those sequence motifs in the order, it is otherwise.

DECISION PREDICATE 5

{ motif (J, s-cytochrome c): search ("CXXCH", J, J1), any (36, 46, J1, J2), match ("MP", J2, -) motif (J, otherwise)

This decision predicate 5 means that when the given sequences J has first and second portions corresponding to the sequence motifs "CXXCH" and "MP", respectively, and when a distance from the first portion to the second portion is given by a symbol number between Min and Max, the sequence J correspond to s-type cytochrome c. However, when the sequence J does not fulfill the conditions, it is otherwise.

Table 5 shows distribution of sequences in the data bank PIR 18.0 corresponding to each of the clauses in each of the decision predicates 4 and 5.

TABLE 5

| Clauses | Total number of sequences | Number of targets | Number of correct sequences |
|---|---|---|---|
| Decision Predicate 4 | | | |
| CXXCH and MP | 6158 | 74 | 25 |
| otherwise | 6084 | 6084 | 6082 |
| Decision Predicate 5 | | | |
| CXXCH and d(36, 46) and MP | 6158 | 25 | 25 |
| otherwise | 6133 | 6133 | 6131 |

When the decision condition does not include a distance information, the description length of the decision condition can be calculated in the similar manner as described in connection with FIG. 2.

When the decision predicate includes a distance information by the "any" predicate, the description length of the distance information should be calculated as a component for determining the description length of the decision condition.

The following three methods are considered for encoding the distance information:

1. Encoding both of the minimum and the maximum values of Min and Max,
2. Encoding the maximum value Max and a difference or distance between the maximum and the minimum values of Max and Min, and
3. Encoding the minimum value Min and a distance or a difference between the maximum and the minimum value of Max and Min.

Since the distance between the maximum and the minimum values Max and Min is always smaller than the maximum value Max, the description length or the bit number necessary for encoding the distance information is made minimum by the use of the third encoding method. Thus, the bit number necessary for encoding the distance information is given by the following formula:

$$\log (Min) + \log (Max - Min).$$

Figure 4:
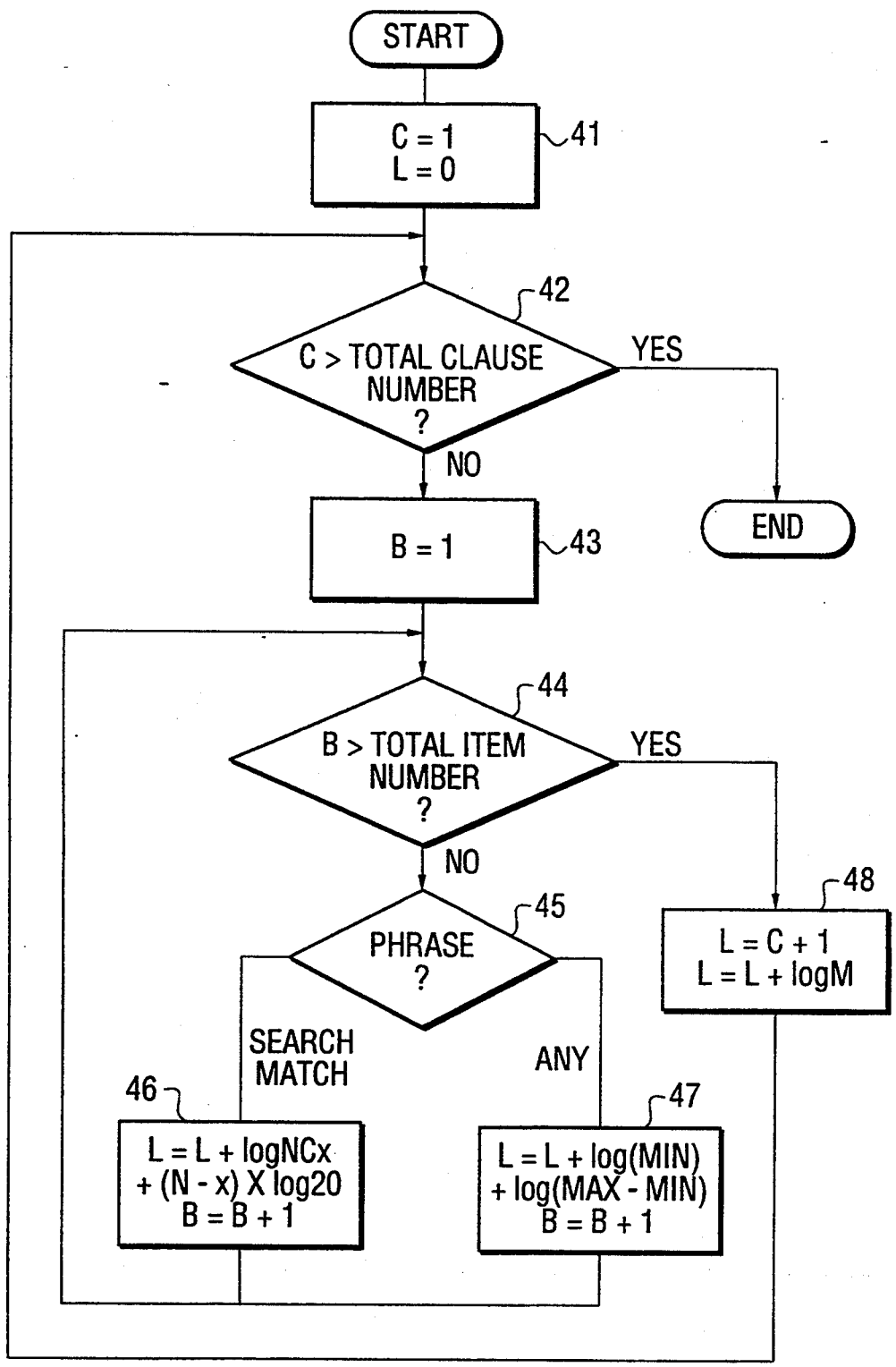
FIG. 4 is a flow chart illustrating another calculation of motifs.

The calculation of the description length of the decision condition is performed according to the flow chart shown in FIG. 4.

It will be understood by comparison of FIG. 2 with FIG. 4 that the flow chart of FIG. 4 is similar to FIG. 2 except for steps 45 and 47. In detail, steps 21-24, 25 and 26 in FIG. 2 is corresponding to steps 41-44, 46 and 48 in FIG. 4, respectively.

At step 45, phrase in each clause is searched. When the phrase is "search" or "match", step proceeds to 46. When the phrase is "any", step proceeds to 47. At step 47, the bit number for the distance information is calculated. That is, the following equations (5) and (6) are calculated.

$$L = L + \log (Min) + \log (Max - Min) \quad (7)$$

$$B = B + 1 \quad (8)$$

Now, description will be made as regards the calculation of the description length of decision condition in the decision predicate 5 with reference to FIG. 4.

The operation of step 41 through step 44 is similar to that of step 21 through step 24 in FIG. 2.

Since the first phrase in the first clause is "search", step proceeds to 46. The first motif pattern "CXXCH" has 5 symbols and the number of "X" is 2. Therefore, the equations (1) and (2) are calculated as follows:

$$L = 0 + \log {}_5C_2 + 3 \log 20 = 16.3$$

$$B = 1 + 1 = 2$$

Then, the second phrase in the first clause is detected as "any" at step 45, and step proceeds to 47. Since Max and Min are 46 and 36, respectively, the equations (7) and (8) are calculated as follows:

$$L = 16.3 + \log 36 + \log (46 - 36) = 24.8$$

$$B = 2 + 1 = 3$$

Thereafter, the third phrase in the first clause is detected as "match" at step 46. Therefore, the step proceeds to 46. The sequence motif "MP" in the third phrase has two symbols and no "X". Therefore, the equations (1) and (2) are calculated as follows:

$$L = 24.8 + \log {}_2C_0 + 2 \log 20 = 33.3$$

$$B = 3 + 1 = 4$$

Thereafter, the step proceeds to 48 from 44, and equations (3) and (4) are calculated as follows:

$$L = 33.3 + \log 1000 = 43.3$$

$$C = 1 + 1 = 2$$

Thereafter, the step again proceeds to 48 through steps 42, 43 and 44 because the total number of items in the final clause is 0. At step 48, equations (3) and (4) are again calculated as follows:ps
$$L = 43.3 + \log 1000 = 53.3$$

$$C = 2 + 1 = 3$$

Thus, the calculation is completed because C exceeds the total clause number, and the description length is obtained as 53.3.

The description length of the precision of the decision condition are calculated in the manner shown in FIG. 3.

Similarly, description length of the decision condition was calculated in connection with the decision predicate 4.

Those results are shown in Table 6.

TABLE 6

| Decision predicate | Decision condition | Description Length | | |
|---|---|---|---|---|
| | | condition | precision | sum |
| 4 | CXXCH and MP | 44.8 | 105.9 | 150.7 |
| 5 | CXXCH and d(36, 46) and MP | 53.3 | 43.0 | 96.3 |

It will be understood from Table 6 that the condition by decision predicate 5 is optimum for discriminating s-type cytochrome c.

Figure 5:
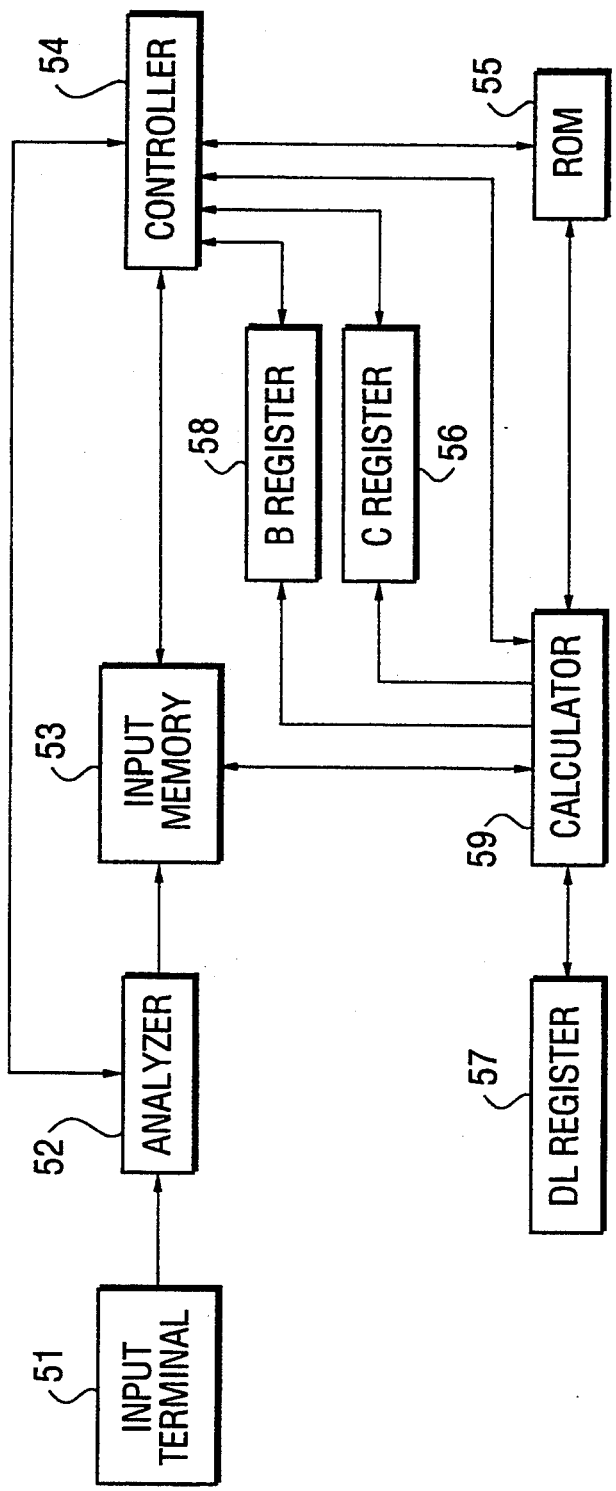
FIG. 5 is a block diagram of a device for executing the calculation illustrated in FIGS. 2, 3, and 4.

Referring to FIG. 5, a device for calculating the description lengths of motifs and precision of the motifs according to the flow charts of FIGS. 2, 3, and 4.

The device comprises an input terminal 51 for inputting a decision predicate. The input terminal 51 is usually a keyboard. The input decision predicate is supplied to an analyzer 52. The analyzer 52 analyzes the input decision predicate and supplies information of the number of clauses, the number of motifs or items in each clause, and the items to an input memory 53. The input memory 53 stores the information as shown in FIG. 6.

When the analyzer 52 receives the input decision predicate, it reports the reception to a controller 54. In response to the report, the controller 54 reads out a program from a read only memory (ROM) 55. The ROM 55 memorizes the program for calculation of the description lengths of the decision condition and the precision according to the flow charts shown in FIG. 2 or FIG. 4 and FIG. 3, respectively. The ROM 55 also memorizes the actual data for correct sequences in the data bank shown in, for example, Tables 1, 3, and 5.

According to the program, the controller 54 controls a C register 56, a DL register 57 and a B register 58 for holding C, L and B, respectively, and calculator 59 for calculating L, B and C, as described in connection with FIGS. 2 or 4 and 3.

The calculator 59 calculates the description length L with reference to the input memory 53 and ROM 55 under control of the controller 54.

What is claimed is:

1. A device for automatically determining an optimum decision condition among a plurality of decision conditions represented as input data signals, said decision condition being used for discrimination of a given symbol sequence as a particular one of a plurality of categories, each of said categories containing a plurality of symbol sequences having common sequence portions as sequence motifs with probabilities, said decision conditions including at least one of said sequence motifs, said device comprising:

an input device, said input device inputting said decision conditions as said input data signals;

an analyzer coupled to receive said input data signals from said input device and to extract calculation information from said input data signal, said analyzer outputting a control signal;

a first memory coupled to said analyzer to receive and store said calculation information;

a second memory storing a set of known data of said categories, said symbol sequences, and said sequence motifs; and a calculator coupled to said first memory and said second memory, said calculator calculates, in response to said control signal and using said calculation information, a plurality of first values representing a corresponding description length of each of said decision conditions, a plurality of second values representing a corresponding description length of a precision of each said decision conditions and a plurality of summed values each representing a sum of one of said first values and one of said second values, said one of said first values and said one of said second values corresponding to a same one of said decision conditions, wherein said calculator compares said plurality of summed values to determine a minimum summed value and indicates said decision condition corresponding to said minimum summed value as said optimum decision condition.

2. A device as recited in claim 1 wherein:

said calculation information comprises a number of clauses, a number of motifs or items in each of said clauses and a number of items in said decision conditions;

said first values represent a number of bits necessary for encoding said category plus a number of bits necessary of encode said motifs or items in said clauses; and said second values represent a number of bits necessary for encoding a probability distribution of a number of said symbol sequences discriminated in each of said clauses in said decision conditions.

3. A device for evaluating efficiency of a plurality of decision conditions used for discrimination of a given symbol sequence as a particular one of a plurality of categories, each of the categories containing a symbol sequences having common sequence portions as sequence motifs with probabilities, said decision conditions including at least one of said sequence motifs and differ from each other in use of said sequence motifs, said device comprising:

input means for sequentially inputting each of said decision conditions as an input data signal;

analyzing means coupled to said input means for analyzing said input data signal to produce an analyzed data signal;

input memory means coupled to said analyzing means for storing said analyzed data signal;

data memory means for storing a set of known data of said categories, said symbol sequences, and said sequence motifs;

calculating means coupled to said input memory means and said data memory means and being responsive to said analyzed data signal for calculating a description length of each of said decision conditions as a first value, said calculating means calculating, as a second value, a description length of a precision of each of said decision conditions from said known data, said calculating means calculating a sum of said first and said second values to produce an evaluation parameter for each of said decision conditions to determine which one of said decision conditions has a minimum evaluation parameter and to indicate said one of said decision conditions as an optimum decision condition; and control means coupled to said input memory means, said data memory means, and said calculating means for controlling operation of said calculating means.

* * * * *

UNITED STATES PATENT AND TRADEMARK OFFICE
CERTIFICATE OF CORRECTION

PATENT NO.   : 5,410,493
DATED        : April 25, 1995
INVENTOR(S)  : KONAGAYA

It is certified that error appears in the above-indentified patent and that said Letters Patent is hereby corrected as shown below:

On title page, after item [22], insert the following:

--[30]  Foreign Application Priority Data
    Sep. 6, 1990 [JP]   Japan        2-236082--.

Signed and Sealed this

Eighteenth Day of June, 1996

Attest:

BRUCE LEHMAN

Attesting Officer

Commissioner of Patents and Trademarks